(12) United States Patent
    Holmqvist

(10) Patent No.: US 8,777,907 B2
(45) Date of Patent: Jul. 15, 2014

(54) MEDICAMENT DELIVERY DEVICE

(75) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 394 days.

(21) Appl. No.: 13/139,293

(22) PCT Filed: Nov. 26, 2009

(86) PCT No.: PCT/EP2009/065901
§ 371 (c)(1),
(2), (4) Date: Aug. 12, 2011

(87) PCT Pub. No.: WO2010/066588
PCT Pub. Date: Jun. 17, 2010

(65) Prior Publication Data
US 2012/0101449 A1    Apr. 26, 2012

Related U.S. Application Data

(60) Provisional application No. 61/122,368, filed on Dec. 13, 2008.

(30) Foreign Application Priority Data

Dec. 12, 2008 (SE) ........................ 0850128

(51) Int. Cl.
*A61M 5/315* (2006.01)
*A61M 5/00* (2006.01)

(52) U.S. Cl.
USPC ........... 604/218; 604/187; 604/220; 604/223; 604/228; 604/229

(58) Field of Classification Search
USPC ................ 604/187, 131, 134–137, 63, 243, 604/218–230, 890.1
See application file for complete search history.

(56) References Cited

U.S. PATENT DOCUMENTS

| 842,631 A * | 1/1907 | Deperdussin ............... 604/62 |
| 4,221,218 A | 9/1980 | Pfleger |
| 5,137,516 A | 8/1992 | Rand et al. |
| 5,298,023 A * | 3/1994 | Haber et al. ................ 604/90 |
| 6,102,896 A * | 8/2000 | Roser ......................... 604/218 |
| 2007/0239114 A1* | 10/2007 | Edwards et al. ........... 604/131 |

FOREIGN PATENT DOCUMENTS

WO    02/076536 A1    10/2002

OTHER PUBLICATIONS

EPO, Int'l Search Report in PCT/EP2009/065901, May 10, 2010.
EPO, Written Opinion in PCT/EP2009/065901, May 10, 2010.

* cited by examiner

*Primary Examiner* — Emily Schmidt
*Assistant Examiner* — Lauren M Peng
(74) *Attorney, Agent, or Firm* — Piedmont Intellectual Property

(57) ABSTRACT

Medicament delivery device comprising: a first housing part (12) having a container holder (14) into which a medicament container (16) can be placed and wherein the container has a front opening with or for a delivery member for delivering the medicament therethrough and a movable stopper (17); a second housing part (38) arranged to be moved between a closed position and an open position in relation to said first housing part (12); a plunger rod (48) having a front end and a rear end, and wherein said plunger rod is arranged parallel beside said container holder when the second housing part is in its closed position; wherein the second housing part comprises resiliently displacement means (50, 52) wherein one of the resiliently displacement means (50) is fixedly connected to said plunger rod, such that when said second housing part (38) is moved from its closed position to its open position, the plunger rod (48) is moved by said resiliently displacement means into a position where the front end of the plunger rod is facing the stopper (17).

15 Claims, 4 Drawing Sheets

MEDICAMENT DELIVERY DEVICE

TECHNICAL AREA

The present invention relates to a medicament delivery device for delivering a dose of medicament.

TECHNICAL BACKGROUND

A large number of medicament delivery devices such as e.g. injectors have been developed during a number of years, having a number of different features that can facilitate in particular the self-administration of medicament. The features include mixing, priming, penetration, injection, retraction of the injection needle and covering of the injection needle, where all or some of the features are performed automatically upon actuation. These features have been combined in many ways in different injectors.

A main design of the above mentioned type of injectors is a generally elongated tubular shape as well as a pen-shape. The advantage with this shape is that it can accommodate elongated plunger rods that act on medicament containers, where the plunger rods are acted upon by spiral springs, such that the components are placed after each other in the longitudinal direction of the injector.

However, this design also means that the injector tends to be rather long, and in particular when a number of the above mentioned features are included in the injector. This can be a major drawback for the users and in particular when the injectors are used publicly and/or if the user has to carry the injector with him. Most users do not want to show others that they use such medicament delivery devices, and therefore there is a general desire that they are as small as possible.

Document U.S. Pat. No. 5,137,516 discloses an injection device that is divided in two parts when not in use, which parts are stored in a housing, which fits into the pocket or handbag of the user. When the injector is to be used, the housing is opened; a syringe administrating device is pulled out and threaded onto a syringe cartridge housing containing a medicament container onto which an injection needle is attached. When threaded together the assembled injector is withdrawn from the housing whereby a rubber septum covering the needle is removed. The injector is now ready for use. The housing could further include compartments for further syringe cartridge housings.

The major drawback with the solution according to U.S. Pat. No. 5,137,516 is that when the injector is ready for use, it is as long as any ordinary injector with plunger rod and injection spring acting on the plunger rod. It is thus not really discrete when it is used, which is a drawback, according to a number of users who do not want to display their devices.

BRIEF DESCRIPTION OF THE INVENTION

The aim of the present invention is to remedy the drawbacks of the state of the art devices and to provide a very compact yet versatile medicament delivery device.

This aim is obtained according to the medicament delivery device comprising the features of the independent patent claim. Preferable embodiments of the invention form the subject of the dependent patent claims.

According to a main aspect of the invention it is characterised by a medicament delivery device comprising a first housing part having a container holder into which a medicament container can be placed and wherein the container has a front opening with or for a delivery member for delivering the medicament therethrough and a movable stopper; a second housing part arranged to be moved between a closed position and an open position in relation to said first housing; a plunger rod having a front end and a rear end, and wherein said plunger rod is arranged parallel beside said container holder when the second housing part is in its closed position; wherein the second housing part comprises resiliently displacement means wherein one of the resiliently displacement means is fixedly connected to said plunger rod, such that when said second housing part is moved from its closed position to its open position, the plunger rod is moved by said resiliently displacement means into a position where the front end of the plunger rod is facing the stopper.

According to a further aspect of the invention, said device further comprises driving force means arranged between the two housing parts;

According to a further aspect of the invention, said device according to further comprises an activation mechanism capable of releasably locking said housing parts.

Preferably said driving force means comprises at least two compression springs.

There are a number of advantages with the present invention. The design according to the invention provides a very compact device because both of the two housing parts slidable in relation to each other whereby the size of the device increases somewhat only when it is used, and both because of the plunger rod that first is placed beside the medicament container and moved and displaced in the right position when the housing parts are slid relative each other. In all a very flexible solution is obtained by having the plunger rod displaced and put in position at the moment a delivery is to be performed.

Preferably the plunger rod is displaced by flexible, resilient arms, which provides a simple yet effective solution containing few components. As an alternative, the flexible resilient arms may be formed by the same material as the plunger rod. As an advantageous solution, the driving force means are tensioned only when the housing parts are slid in relation to each other. This means that the driving force means, such as compression springs are not left in tensioned states for long time periods when stored. Preferably there are two springs in order to provide an even force when the two housing parts are slid in relation to each other during delivery. Preferably an activation mechanism is arranged to lock the two housing parts when the springs are tensioned, which puts the medicament delivery device in order for delivery. The activation mechanism may then be activated by e.g. pressing a button, whereby the housing parts are released from each other and a delivery is performed.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 2:
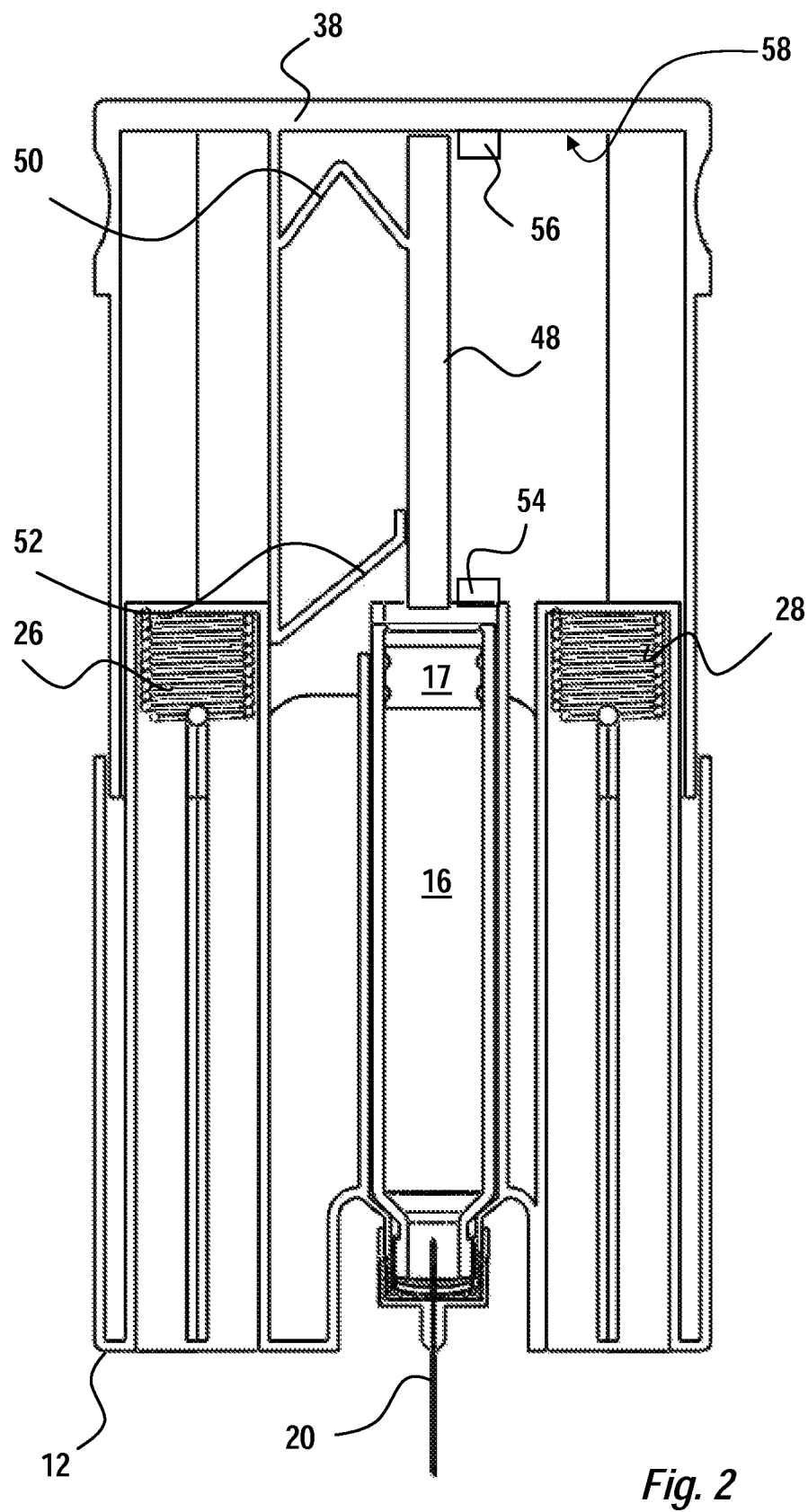
FIG. 2 is a cross-sectional side view of the device according to FIG. 1 when armed.
Figure 3:
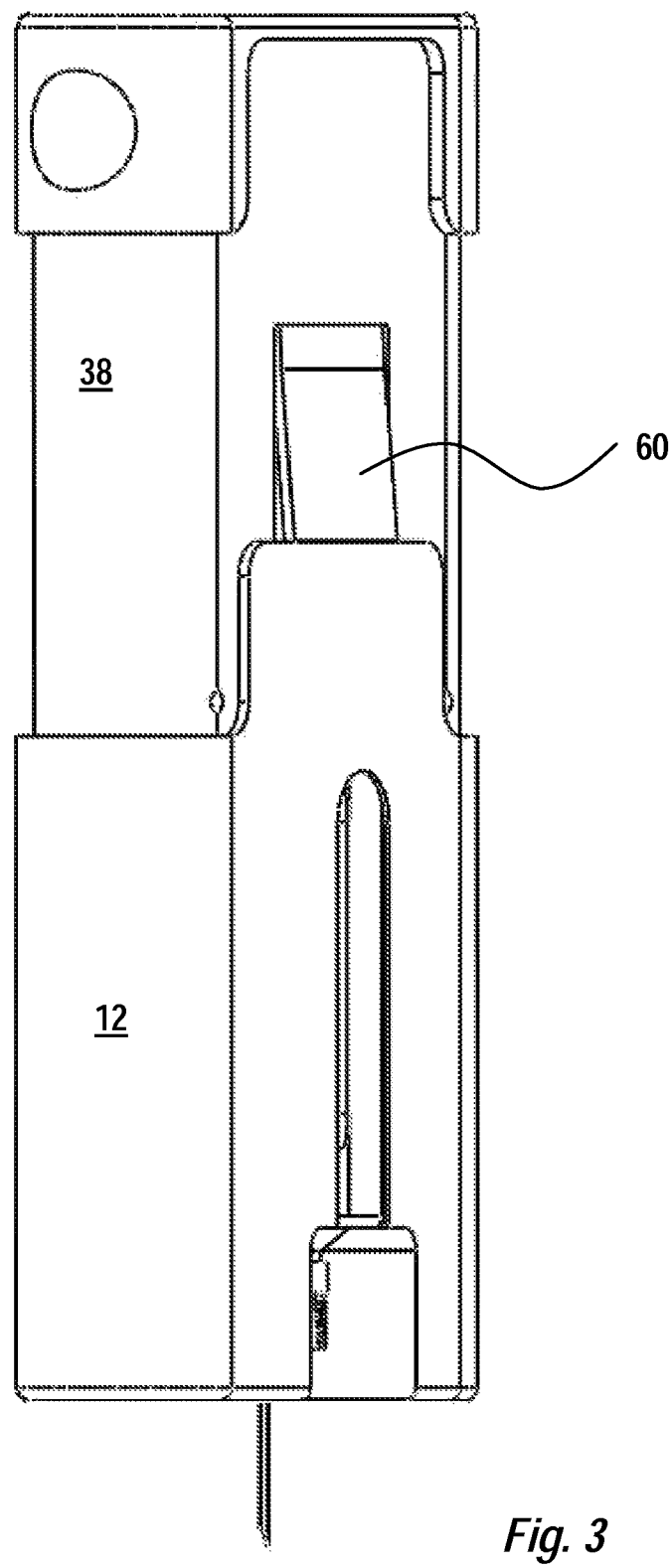
FIG. 3 is a perspective view of the device in the position of FIG. 2.
Figure 4:
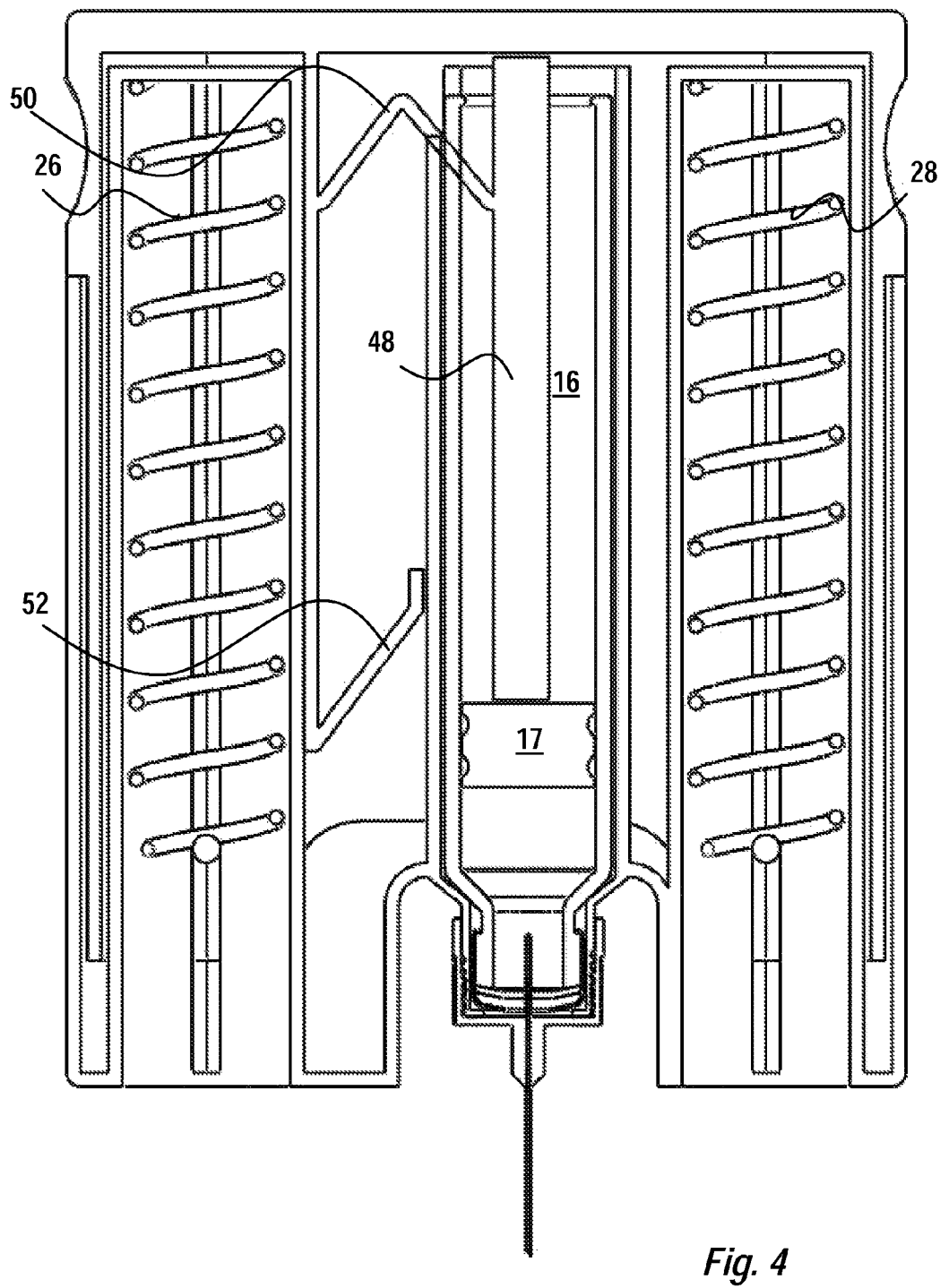
FIG. 4 is a cross-sectional side view of the device according to FIG. 1 when the delivery is completed.

The medicament delivery device of the present invention comprises a first housing part 12 having a container holder 14 into which a medicament container 16 can be placed and wherein the container has a front opening with or for a delivery member, e.g. a needle as shown in FIGS. 2-4, for delivering the medicament therethrough and a movable stopper 17; a second housing part 38 arranged to be moved between a closed position and an open position in relation to said first housing 12; a plunger rod 48 having a front end and a rear end, and wherein said plunger rod is arranged parallel beside said container holder when the second housing part is in its closed position; wherein the second housing part comprises resiliently displacement means 50, 52 wherein one of the resiliently displacement means 50 is fixedly connected to said plunger rod, such that when said second housing part 38 is moved from its closed position to its open position, the plunger rod 48 is moved by said resiliently displacement means into a position where the front end of the plunger rod is facing the stopper 17.

In a first embodiment (not shown), the first housing part is arranged with a central elongated compartment forming the container holder 14, and with a neck 18, onto which neck, the delivery member e.g. a needle, may be attached in a suitable from, e.g. by threading or by pushing. The first and second housing parts are guided in relation to each other by sliding means of the second housing part fits into guide slots of the first housing part. A further compartment 46 is arranged parallel beside the container holder for housing the plunger rod 48.

The device of the first embodiment (not shown) is intended to function as follows. When the device is delivered to the user, the second housing part is in its closed position, i.e. the two housing parts 12, 38 are pushed together. The plunger rod 48 is positioned in the further compartment 46, parallel beside said container holder, and is pushed by the flexible arms 50, 52 against an outer surface of the container holder 14. When the patient is to take a dose of medicament, he/she attaches a delivery member 20 as e.g. a needle on the neck 18 of the container holder 14.

The second housing part 38 is now manually moved upwards. The movement of the second housing part 38 also causes the plunger rod 48 to be lifted and it slides along the outer surface of the container holder 14 until it comes to a certain position when the plunger rod 48 is moved out of contact from the outer surface of the container holder 14. The flexible arms 50, 52 then displace the plunger rod sideways to a position when its front end faces the stopper, i.e. it is in line with the longitudinal axis of the medicament container 16. Preferably some sort of stop ledges 54, 56 are arranged to guide the plunger rod into this position. The device is now ready for delivery.

The user then positions the delivery member on the delivery site, e.g. penetrates an injection site with an injection needle. After this, the second hosing part is manually depressed by the user whereby an inner end surface 58 of the second housing part is brought in contact with the rear end surface of the plunger rod 48 and due to the force applied by the user on the second housing part, the plunger rod 48 is forced downwards. This movement causes the stopper 17 to be moved inside the medicament container, whereby a dose of medicament is delivered through the delivery member. When the medicament delivery is completed the device can be withdrawn from the delivery site. The device may further be arranged with a means for opening replacing the used medicament container with a new one for subsequent delivery.

Figure 1:
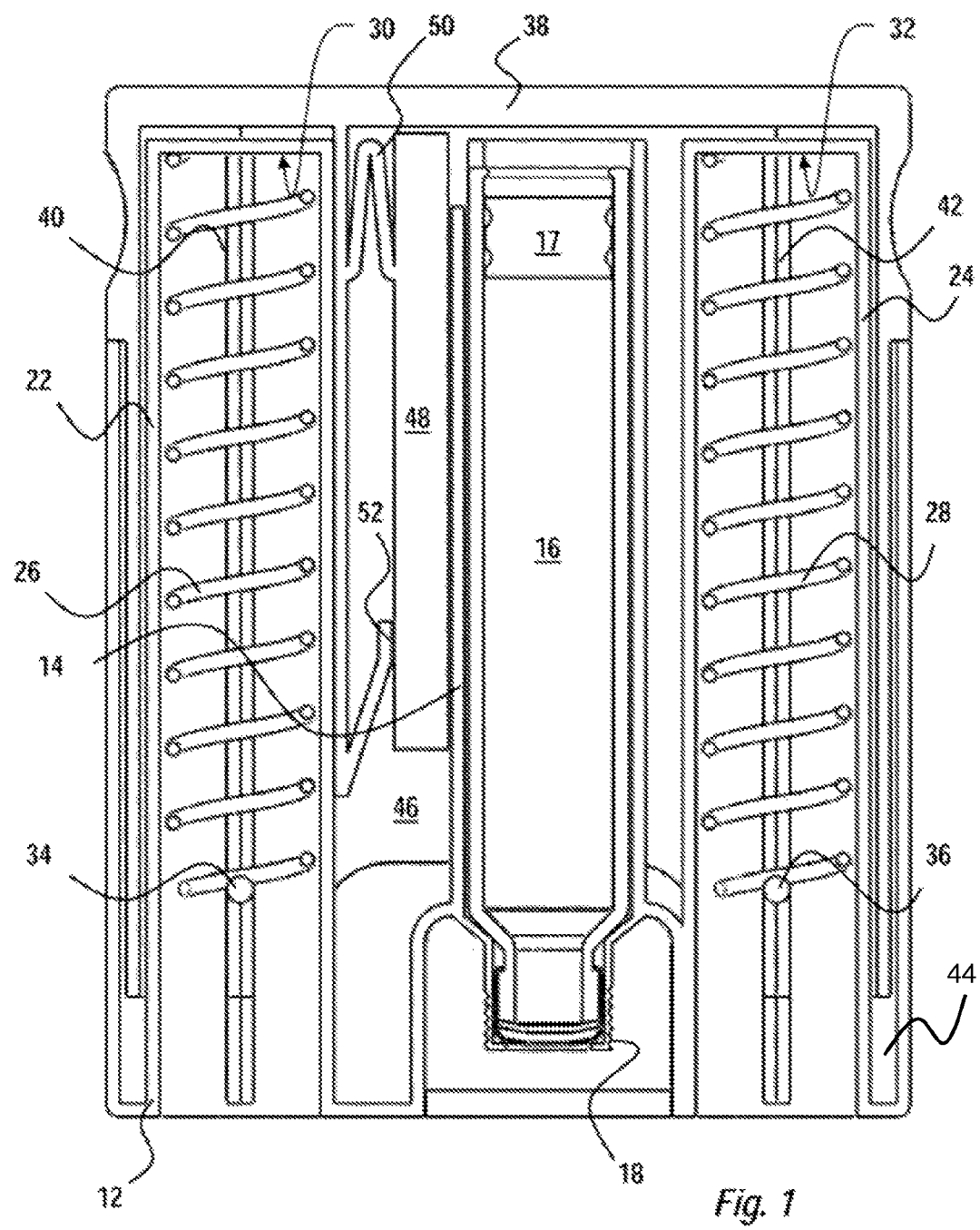
FIG. 1 is a cross-sectional side view of an embodiment of the present invention in an initial state.

In a second embodiment shown in FIGS. 1-4, the first housing part is arranged with a central elongated compartment forming the container holder 14, and with a neck 18, onto which neck, the delivery member e.g. a needle, may be attached in a suitable from, e.g. by threading or by pushing. The first and second housing parts are guided in relation to each other by sliding means of the second housing part fits into guide slots of the first housing part. On the side of the central compartment two elongated tubular compartments 22, 24 are arranged generally parallel with the container holder 14. Each side compartment is arranged with driving force means 26, 28, e.g. at least two compression springs as shown in FIGS. 1, 2, and 4. Said driving force means are arranged between the two housing parts 12, 38; positioned between an end wall 30, 32 of the side compartments and a respective stop pin 34, 36. The stop pins are in turn attached to the second housing part 38 and protrude into the side compartments through elongated slots 40, 42. The first and second housing parts are guided in relation to each other in that a lower part of the wall of the second housing part fits into guide slots 44 of the first housing part.

In the second embodiment, the driving force means are arranged in a non-compressed state when said second housing is in the closed position; and are arranged to be moved from the non-compressed state to a compressed state when said second housing is moved from its closed position to its open position.

A further compartment 46 is arranged between the container holder 14 and one of the side compartments 22. This further compartment houses the plunger rod 48. The plunger rod 48 is fixedly attached to the second housing part via the displacement means, in the FIGS. 1-4, shown as a resilient and flexible arm 50. The displacement means further comprises a further resilient and flexible arm 52 which is further fixedly attached to the second housing part, the function of which will be described below.

In the embodiment shown in the FIGS. 1-4, the medicament delivery device further comprises an activation mechanism 60, FIG. 3, capable of releasably locking said housing parts 12, 38 when said second housing is moved from its closed position to its open position. The activation mechanism 60 is arranged to the second housing part, which will be described in detail below.

The device of the second embodiment shown in the FIGS. 1-4 is intended to function as follows. When the device is delivered to the user, as shown in FIG. 1, the second housing part is in its closed position, i.e. the two housing parts 12, 38 are pushed together and the springs 26, 28 are in non-tensioned states. The plunger rod 48 is positioned in the further compartment 46, parallel beside said container holder, and is pushed by the flexible arms 50, 52 against the outer surface of the container holder 14. When the patient is to take a dose of medicament, he/she attaches a delivery member 20 as e.g. a needle on the neck 18 of the container holder 14.

The second housing part 38 is now manually lifted whereby the springs 26, 28 will be tensioned because the stop pins 34, 36 are moved upwards in the slots 40, 42 of the side compartments 22, 24. The movement of the second housing part 38 also causes the plunger rod 48 to be lifted and it slides along the outer surface of the container holder 14 until it comes to a certain position when the plunger rod 48 is moved out of contact from the outer surface of the container holder 14. The flexible arms 50, 52 then displace the plunger rod sideways to a position when its front end faces the stopper, i.e. it is in line with the longitudinal axis of the medicament container 16. Preferably some sort of stop ledges 54, 56 are arranged to guide the plunger rod into this position, FIG. 2. When the plunger rod is positioned, the activation mechanism 60 releasably locks the second housing part to the first housing part by at least one flexible wall part of the second housing part which comes in contact with the upper edge of the first housing part, FIG. 3. The device is now ready for delivery.

The user then positions the delivery member on the delivery site, e.g. penetrates an injection site with an injection needle. After this the activation mechanism 60 is manually activated by the user whereby the second housing part 38 is released from the first housing part 12. An inner end surface 58 of the second housing part is brought in contact with the rear end surface of the plunger rod 48 and due to the force of the springs 26, 28 the plunger rod 48 is forced downwards. This movement causes the stopper 17 to be moved inside the medicament container, whereby a dose of medicament is delivered through the delivery member. When the medicament delivery is completed the device can be withdrawn from the delivery site. The device may further be arranged with a means for opening replacing the used medicament container with a new one for subsequent delivery. Further the activation mechanism may have different designs than the one described with the second embodiment.

In a third embodiment (not shown), the driving force means 26, 28 are arranged in a compressed state when said second housing is in the closed position, and are arranged to be moved from the compressed state to a non-compressed state when said second housing is manually moved from its closed position to its open position. Further, the device of the third embodiment further comprises an activation mechanism capable of releasably locking said housing parts 12, 38 when said second housing is in its closed position. The activation mechanism may be achieved as e.g. a flexible tongue with a locking means either on the first or the second housing part, wherein said locking means is adapted to releasably co-act with a corresponding locking means on either the second or the first housing part.

The device of the third embodiment is intended to function as follows. When the device is delivered to the user, the second housing part is in its closed position, i.e. the two housing parts 12, 38 are pushed together and the springs 26, 28 are in tensioned states. The plunger rod 48 is positioned in the further compartment 46, parallel beside said container holder, and is pushed by the flexible arms 50, 52 against the outer surface of the container holder 14. When the patient is to take a dose of medicament, he/she attaches a delivery member 20 as e.g. a needle on the neck 18 of the container holder 14.

The activation mechanism 60 is manually activated by the user whereby the second housing part 38 is released from the first housing part 12 and due to the force of the springs 26, 28, the second housing part is moved upwards. The movement of the second housing part 38 also causes the plunger rod 48 to be lifted and it slides along the outer surface of the container holder 14 until it comes to a certain position when the plunger rod 48 is moved out of contact from the outer surface of the container holder 14. The flexible arms 50, 52 then displace the plunger rod sideways to a position when its front end faces the stopper, i.e. it is in line with the longitudinal axis of the medicament container 16. Preferably some sort of stop ledges are arranged to guide the plunger rod into this position. When the plunger rod is positioned, the device is now ready for delivery. The user then positions the delivery member on the delivery site, e.g. penetrates an injection site with an injection needle. After this, the second hosing part is manually depressed by the user whereby an inner end surface 58 of the second housing part is brought in contact with the rear end surface of the plunger rod 48 and due to the force applied by the user on the second housing part, the plunger rod 48 is forced downwards. This movement causes the stopper 17 to be moved inside the medicament container, whereby a dose of medicament is delivered through the delivery member. When the medicament delivery is completed the device can be withdrawn from the delivery site. The device may further be arranged with a means for opening replacing the used medicament container with a new one for subsequent delivery. Further the activation mechanism may have different designs than the one described with the third embodiment.

The wording medicament container may embrace several different types of containers such as cartridges, ampoules, syringes, vials, aerosol containers, just to mention a few. In that respect the present invention could also be used with other types of delivery devices such as powder or aerosol inhalers as well as nebulizers, with delivery members as nozzles, mouth pieces, or nasal pieces capable of delivering a dose of medicament to be inhaled by the patient.

It is further to be understood that other types of driving force means can be used for the delivery of the medicament to a patient, such as clock springs, volute springs, pneumatic or hydraulic springs or any other type of non-electric power source suitable for the intended use according to the present invention.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
a first housing part having a container holder configured for a medicament container that has a front opening for a delivery member for delivering a medicament therethrough and a movable stopper;
a plunger rod having a front end and a rear end; and
a second housing part, comprising resilient displacement devices, wherein one of the resiliently displacement devices is fixedly connected to the plunger rod;
wherein the first and second housing parts are guided in relation to each other by a slider of the second housing part fitting into guide slots of the first housing part; the second housing part is arranged to be moved between a closed position, in which the first and second housing parts are pushed together when the device is delivered to a user, and an open position in relation to the first housing part; the plunger rod is arranged parallel beside the container holder when the second housing part is in the closed position; and when the second housing part is moved from the closed position to the open position, the plunger rod is moved sideways by the resilient displacement devices into a position where a front end of the plunger rod faces the stopper and the second housing part can be depressed, whereby an inner end surface of the second housing part is brought into contact with the rear end surface of the plunger rod and the plunger rod is forced forward due to force applied to the second housing part.

2. The medicament delivery device of claim 1, wherein the second housing part is arranged to be manually moved from the open position to the closed position, such that the plunger rod acts on the stopper for dispensing the medicament.

3. The medicament delivery device of claim 1, further comprising a driver mechanism, comprising at least two compression springs arranged between the first and second housing parts.

4. The medicament delivery device of claim 3, further comprising an activation mechanism configured for releasably locking the first and second housing parts when the second housing part is moved from the closed position to the open position.

5. The medicament delivery device of claim 4, wherein the at least two compression springs are configured for acting on the plunger rod for dispensing the medicament when the activation mechanism releases the first and second housing parts when activated manually.

6. The medicament delivery device of claim 3, wherein the at least two compression springs are in a non-compressed state when the second housing part is in the closed position.

7. The medicament delivery device of claim 6, further comprising an activation mechanism configured for releasably locking the first and second housing parts when the second housing part is moved from the closed position to the open position.

8. The medicament delivery device of claim 7, wherein the at least two compression springs are configured for acting on the plunger rod for dispensing the medicament when the activation mechanism releases the first and second housing parts when activated manually.

9. The medicament delivery device of claim 6, wherein the at least two compression springs are arranged to be moved from the non-compressed state to a compressed state when the second housing part is moved from the closed position to the open position.

10. The medicament delivery device of claim 9, further comprising an activation mechanism configured for releasably locking the first and second housing parts when the second housing part is moved from the closed position to the open position.

11. The medicament delivery device of claim 10, wherein the at least two compression springs are configured for acting on the plunger rod for dispensing the medicament when the activation mechanism releases the first and second housing parts when activated manually.

12. The medicament delivery device of claim 3, wherein the at least two compression springs are arranged in a compressed state when the second housing part is in the closed position.

13. The medicament delivery device of claim 12, wherein the at least two compression springs are arranged to be moved from the compressed state to a non-compressed state when the second housing part is moved from the closed position to the open position.

14. The medicament delivery device of claim 12, further comprising an activation mechanism configured for releasably locking the first and second housing parts when the second housing part is in the closed position.

15. The medicament delivery device of claim 14, wherein the second housing part is arranged to be manually moved from the open position to the closed position, such that the plunger rod acts on the stopper for dispensing the medicament.

* * * * *